(12) United States Patent  (10) Patent No.: US 11,317,855 B2
Kim et al.  (45) Date of Patent: May 3, 2022

(54) SPASTICITY EVALUATION DEVICE, METHOD AND SYSTEM

(71) Applicant: DAEGU GYEONGBUK INSTITUTE OF SCIENCE AND TECHNOLOGY, Daegu (KR)

(72) Inventors: Jong Hyun Kim, Daegu (KR); Seo Young Choi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 406 days.

(21) Appl. No.: 16/461,535

(22) PCT Filed: Nov. 18, 2016

(86) PCT No.: PCT/KR2016/013319
§ 371 (c)(1),
(2) Date: Nov. 4, 2019

(87) PCT Pub. No.: WO2018/092944
PCT Pub. Date: May 24, 2018

(65) Prior Publication Data
US 2020/0054275 A1  Feb. 20, 2020

(51) Int. Cl.
*A61B 5/00* (2006.01)
*A61B 5/107* (2006.01)
*A61B 5/11* (2006.01)

(52) U.S. Cl.
CPC .......... *A61B 5/4519* (2013.01); *A61B 5/1071* (2013.01); *A61B 5/1121* (2013.01);
(Continued)

(58) Field of Classification Search
CPC ... A61B 5/4519; A61B 5/1071; A61B 5/1121; A61B 2562/0219; A61B 5/1124;
(Continued)

(56) References Cited

U.S. PATENT DOCUMENTS

2009/0118649 A1  5/2009 Cabrera et al.
2013/0303947 A1* 11/2013 Gamet ................. A61B 5/1107
    600/595
2016/0317066 A1  11/2016 Wang et al.

FOREIGN PATENT DOCUMENTS

JP  2015-217126 A  12/2015
KR  10-1181077 B1  9/2012
    (Continued)

OTHER PUBLICATIONS

Machine translation of KR 101656940 B1 (Year: 2021).*
Korean Office Action dated Nov. 20, 2020 issued in corresponding Korean Appln. No. 10-2019-7015055.

*Primary Examiner* — Sean P Dougherty
*Assistant Examiner* — Kyle W. Kretzer
(74) *Attorney, Agent, or Firm* — Harness, Dickey & Pierce, P.L.C

(57) ABSTRACT

System comprises a first sensing unit, attached to a proximal portion of a human body with a joint of the human body as a reference, for measuring an acceleration of the proximal portion or an angular velocity of the proximal portion; a second sensing unit, attached to a distal end portion of the human body, for measuring an acceleration of the distal end portion or the angular velocity of the distal end portion; a processing unit for determining an angle of the joint between the proximal portion and the distal end portion on the basis of the measured acceleration or the measured angular velocity and determining a spasticity time point at which resistance to motion of the distal end portion is received; and a display unit for displaying spasticity evaluation information for a spasticity evaluation on the basis of the angle of the joint and the spasticity time point.

19 Claims, 11 Drawing Sheets

(52) U.S. Cl.
CPC .......... *A61B 5/6844* (2013.01); *A61B 5/7242* (2013.01); *A61B 5/746* (2013.01); *A61B 5/7425* (2013.01); *A61B 2562/0219* (2013.01)

(58) Field of Classification Search
CPC ... A61B 5/4082; A61B 5/6844; A61B 5/7242; A61B 5/7425; A61B 5/746
See application file for complete search history.

(56) References Cited

FOREIGN PATENT DOCUMENTS

| KR | 10-2013-0034245 A | 4/2013 |
|---|---|---|
| KR | 10-2016-0033828 A | 3/2016 |
| KR | 10-2016-0058847 A | 5/2016 |
| KR | 10-2016-0097044 A | 8/2016 |
| KR | 10-1656940 B1 | 9/2016 |
| KR | 101656940 B1 * | 9/2016 |

* cited by examiner

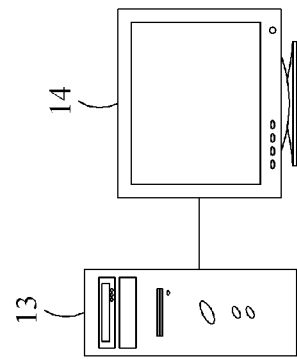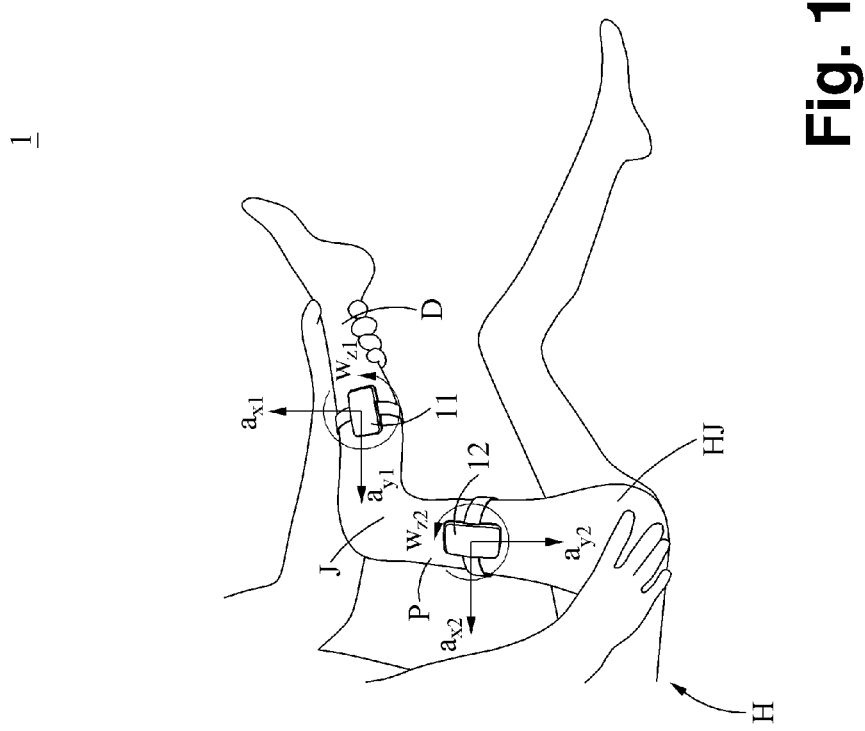
Fig. 1

Velocity to stretch (V)

| | | |
|---|---|---|
| V1 | | As slow as possible |
| V2 | | Speed of the limb segment falling (> natural drop) |
| V3 | | As fast as possible |

V1 is used to measure the passive range of Motion. (PROM). Only V2 and V3 are used to rate spasticity

Spasticity Angle

| | |
|---|---|
| R1 | Angle of catch seen at Velocity V2 or V3 |
| R2 | Full range of motion achieved when muscle is at rest and tested at V1 velocity |

Quality of muscle reaction (X)

| | |
|---|---|
| 0 | No resistance throughout passive movement |
| 1 | Slight resistance throughout, with no clear catch at a precise angle |
| 2 | Clear catch at a precise angle, followed by release |
| 3 | Fatigable clonus (<10secs) occurring at a precise angle |
| 4 | Unfatigable clonus (>10secs) occurring at a precise angle |
| 5. | Joint Immobile |

Angle of muscle reaction (Y)

Measure relative to the position of minimal stretch of the muscle (corresponding at angle)

Fig. 3

SPASTICITY EVALUATION DEVICE, METHOD AND SYSTEM

TECHNICAL FIELD

Example embodiments relate to a spasticity evaluation device, method, and system.

BACKGROUND ART

Spasticity refers to muscle tension that increases in proportion to a rate of muscle stretching due to over-excitation of stretch reflex. The stretch reflex refers to a condition in which, when a skeletal muscle is continuously stretched, tension increases due to a muscle contraction occurring reflexively or resistantly in response to the stretched muscle.

A modified tardieu scale (MTS), a modified ashworth scale (MAS), and the like may be used in a clinical field of application as an evaluation tool to evaluate such spasticity. The MTS is a clinical measure used to measure muscle spasticity, and is obtained by recording and measuring a degree of spasticity and an angle of resistance point at which spasticity is felt when limbs, for example, an arm and a leg, are moved passively by an operator at a relatively low speed or high speed.

For example, Korean Patent Registration No. 10-1181077 discloses an apparatus for evaluation of hamstring tightness or flexibility, and a method thereof.

DISCLOSURE OF INVENTION

Technical Goals

An aspect provides a clinically favorable spasticity evaluation device, method, and system to which an evaluation tool used in a clinical field of application is applied.

An aspect also provides a spasticity evaluation device, method, and system that may improve accuracy and reliability of evaluation of spasticity using an inertial sensor.

An aspect also provides a spasticity evaluation device, method, and system that may assist a user with an intuitive determination using visual biofeedback.

Technical Solutions

According to an example embodiment, there is provided a spasticity evaluation system including a first sensor attached to a distal end portion of a human body from a joint of the body and configured to measure an acceleration or an angular velocity of the distal end portion, a second sensor attached to a proximal portion of the body from the joint of the body and configured to measure an acceleration or an angular velocity of the proximal portion, a processor configured to determine an angle of the joint formed between the distal end portion and the proximal portion based on the measured accelerations or the measured angular velocities, and determine a spasticity time at which resistance is applied to a movement of the distal end portion, and a display configured to display spasticity evaluation information to be used to evaluate spasticity based on the angle of the joint and the spasticity time.

When the measured accelerations include an acceleration occurring in a direction intersecting a sagittal plane of the body, the processor may determine the angle of the joint by performing a rotation transformation matrix on the measured accelerations.

The processor may include a quasi-static mode in which the angle of the joint is determined based on the measured accelerations and a dynamic mode in which the angle of the joint is determined based on the measured angular velocities, and may determine the quasi-static mode or the dynamic mode based on the measured accelerations and the measured angular velocities.

When a magnitude of the measured accelerations is in a first range and a magnitude of the measured angular velocities is in a second range, the processor may determine the quasi-static mode.

When the quasi-static mode is determined, the processor may obtain a first angle based on a first acceleration on the sagittal plane of the body among accelerations measured by the first sensor and a second acceleration in a direction intersecting a direction of the first acceleration on the sagittal plane, obtain a second angle based on a fourth acceleration on the sagittal plane among accelerations measured by the second sensor and a fifth acceleration in a direction intersecting a direction of the fourth acceleration on the sagittal plane, and determine the angle of the joint based on the obtained first angle and the obtained second angle.

When the dynamic mode is determined, the processor may obtain a first angular displacement by performing an integration on angular velocities measured by the first sensor, obtain a second angular displacement by performing an integration on angular velocities measured by the second sensor, and determine the angle of the joint based on the obtained first angular displacement and the obtained second angular displacement.

The processor may further calculate a magnitude of a variation in angular velocity measured by the first sensor or a magnitude of a variation in angular velocity measured by the second sensor, and determine, to be the spasticity time, a point in time corresponding to a variation with a maximum magnitude among the calculated magnitudes of the variation.

The processor may include a first velocity mode in which an angle of the joint with a maximum magnitude is determined to be an operating velocity when the measured angular velocities are a first velocity, and a second velocity mode in which an angle of the joint at the spasticity time is determined to be a catch angle when the measured angular velocities are a second velocity which is greater than the first velocity.

The processor may determine a spasticity evaluation score in the spasticity evaluation information based on the operating angle, the catch angle, and the spasticity time.

The first sensor may measure an acceleration in a length direction of the distal end portion on the sagittal plane of the body, an acceleration in a direction intersecting the length direction of the distal end portion on the sagittal plane, and an angular velocity in a direction intersecting the sagittal plane.

The processor may determine an attachment state of the first sensor and an attachment state of the second sensor based on the measured accelerations or the measured angular velocities, and the display may display a warning signal relating to an erroneous sensor attachment based on the determined attachment state of the first sensor and the determined attachment state of the second sensor.

The processor may determine a velocity of the joint based on the measured accelerations or the measured angular velocities, and the display may display whether the velocity of the joint reaches a target velocity within a preset margin of error.

According to another example embodiment, there is provided a spasticity evaluation device including a first sensor attached to a distal end portion of a human body from a joint of the body and configured to obtain a first measurement value including an acceleration in a first direction intersecting a length direction of the distal end portion, an acceleration in a second direction intersecting the first direction, or an angular velocity in a third direction intersecting each of the first direction and the second direction, a second sensor attached to a proximal portion of the body from the joint of the body and configured to obtain a second measurement value including an acceleration in a fourth direction intersecting a length direction of the proximal portion, an acceleration in a fifth direction intersecting the fourth direction, or an angular velocity in a sixth direction intersecting each of the fourth direction and the fifth direction, and a display connected to the first sensor and the second sensor and configured to display spasticity evaluation information to be used to evaluate spasticity based on the first measurement value and the second measurement value.

The display may display, as a velocity of the joint, a value obtained by calculating the angular velocity in the third direction and the angular velocity in the sixth direction.

The display may display the velocity of the joint in real time, and display whether the velocity of the joint reaches a target velocity.

The first measurement value may further include an acceleration in the third direction, and the second measurement value may further include an acceleration in the sixth direction, and the display may display whether each of a magnitude of the acceleration in the third direction and a magnitude of the acceleration in the sixth direction is included in a preset magnitude range.

According to still another example embodiment, there is provided a spasticity evaluation method including measuring an acceleration or an angular velocity of a distal end portion of a human body from a joint of the body, and an acceleration or an angular velocity of a proximal portion of the body from the joint of the body, determining a quasi-static mode or a dynamic mode based on the measured accelerations and the measured angular velocities, determining an angle of the joint based on an acceleration measured in the quasi-static mode and determining an angle of the joint based on an angular velocity measured in the dynamic mode, determining a spasticity time at which resistance is applied to a movement of the distal end portion, and determining a spasticity evaluation score based on the determined angle of the joint and the determined spasticity time.

After the measuring of the acceleration or the angular velocity of the distal end portion, and the acceleration or the angular velocity of the proximal portion, the spasticity evaluation method may further include displaying a warning signal relating to an erroneous sensor attachment, when each of an acceleration in a direction intersecting a sagittal plane of the body among measured accelerations of the distal end portion and an acceleration in a direction intersecting the sagittal plane among measured accelerations of the proximal portion is out of a preset magnitude range.

After the displaying of the warning signal, the spasticity evaluation method may further include determining an angular velocity of the joint by calculating the measured angular velocity of the distal end portion and the measured angular velocity of the proximal portion, and displaying whether the determined angular velocity of the joint reaches a target velocity.

Before the determining of the quasi-static mode or the dynamic mode, the spasticity evaluation method may further include performing a preset rotation transformation matrix on each of the measured acceleration of the distal end portion and the measured acceleration of the proximal portion, when each of an acceleration component in a direction intersecting the sagittal plane of the body among measured accelerations of the distal end portion and an acceleration component in a direction intersecting the sagittal plane among measured accelerations of the proximal portion is out of a preset magnitude range.

Advantageous Effects

According to example embodiments described herein, a spasticity evaluation device, method, and system may be clinically favorable by an application of an evaluation tool used in a clinical field of application.

According to example embodiments described herein, a spasticity evaluation device, method, and system may improve accuracy and reliability of evaluation of spasticity using an inertial sensor.

According to example embodiments described herein, a spasticity evaluation device, method, and system may assist a user with an intuitive determination using visual biofeedback.

Advantageous effects of the spasticity evaluation device, method, and system are not limited to what has been described in the foregoing, and other effects may be explicitly understood by those skilled in the art from the following description.

BRIEF DESCRIPTION OF DRAWINGS

FIG. 1 is a diagram illustrating an example of a spasticity evaluation system according to an example embodiment.

FIG. 3 is a diagram illustrating an example of a spasticity evaluation method according to an example embodiment.

BEST MODE FOR CARRYING OUT THE INVENTION

Figure 2:
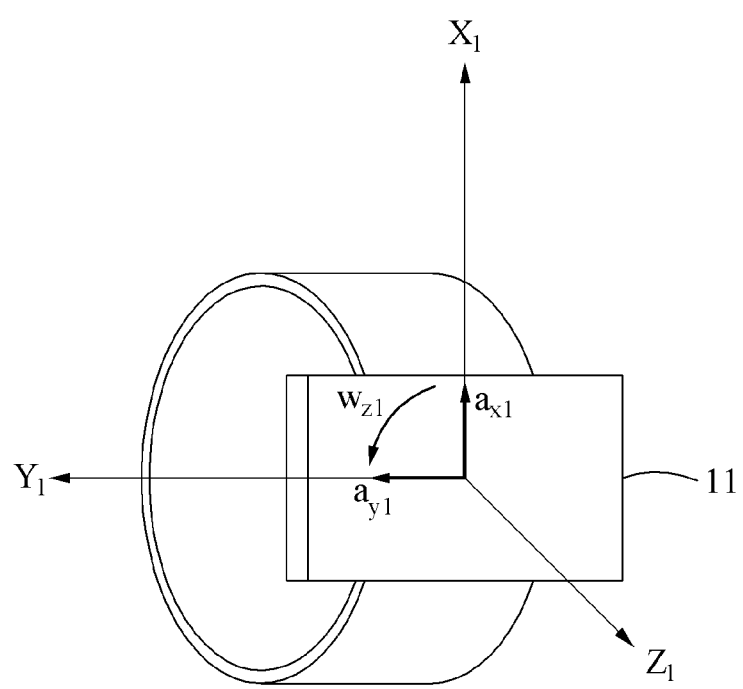
FIG. 2 is a diagram illustrating an example of a sensor unit according to an example embodiment.
Figure 4:
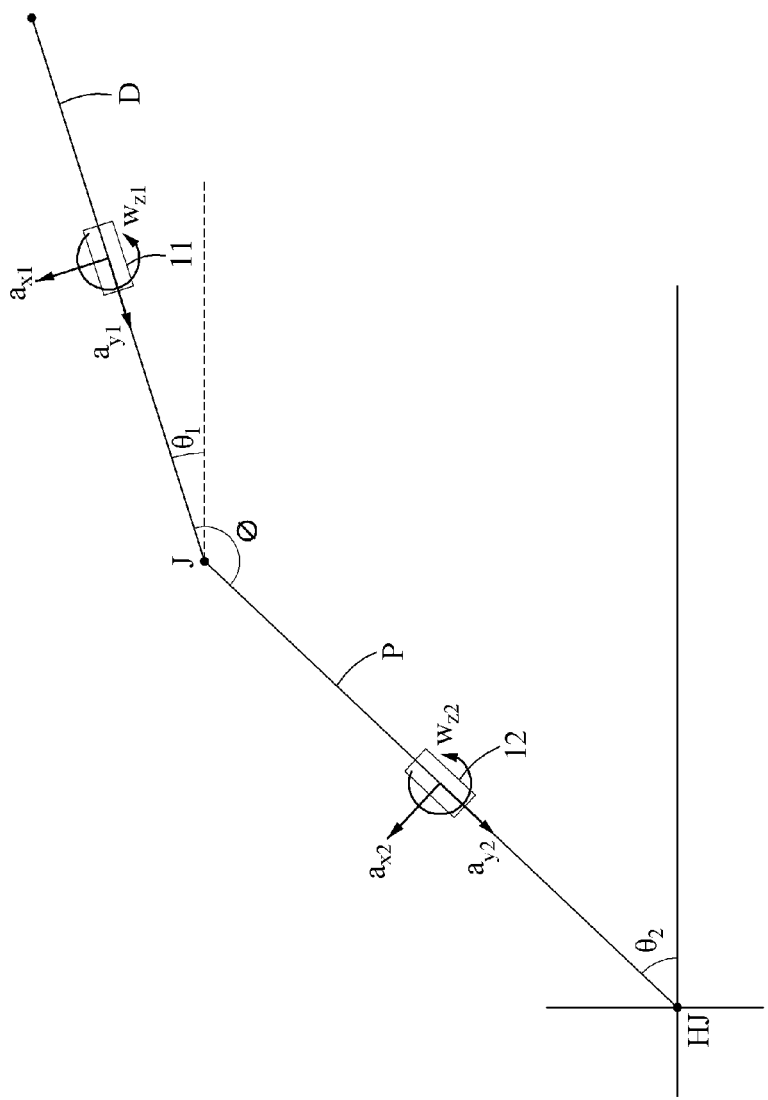
FIG. 4 is a diagram illustrating an example of determining a joint angle according to an example embodiment.
Figure 5:
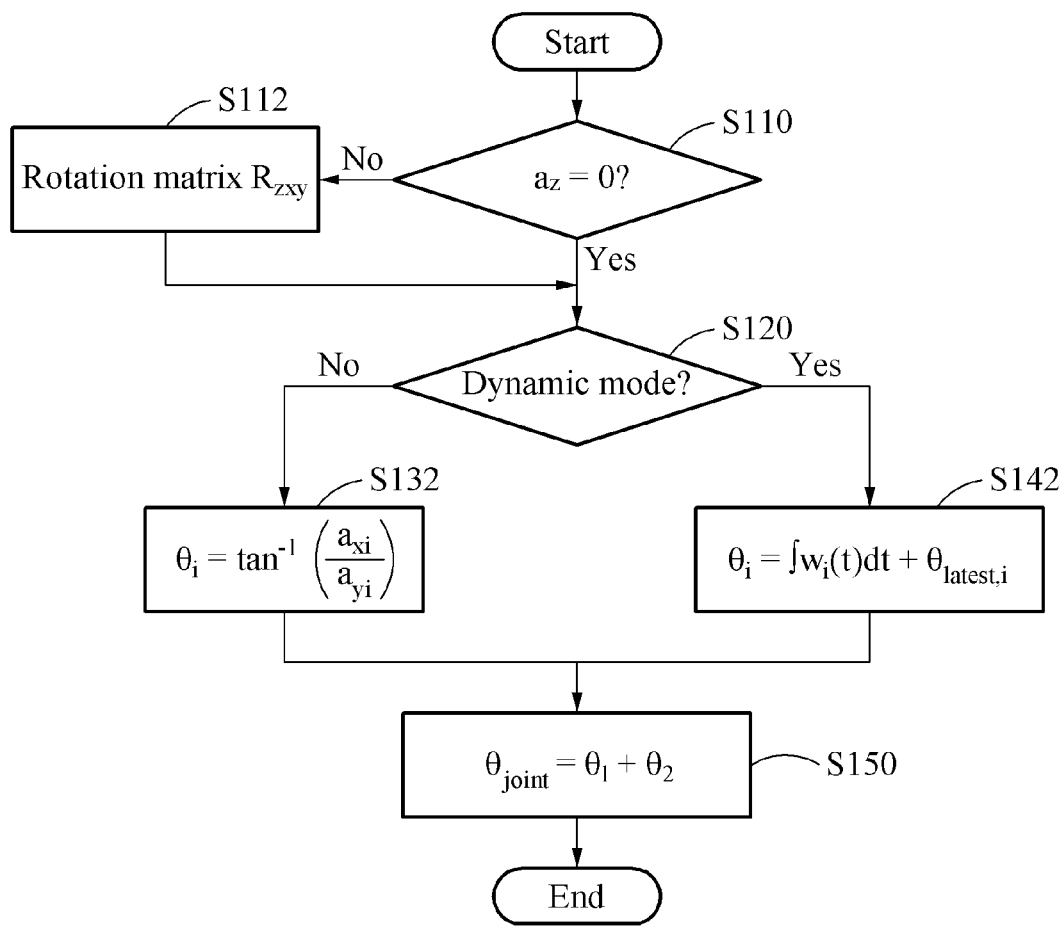
FIG. 5 is a flowchart illustrating an example of determining a joint angle according to an example embodiment.
Figure 6:
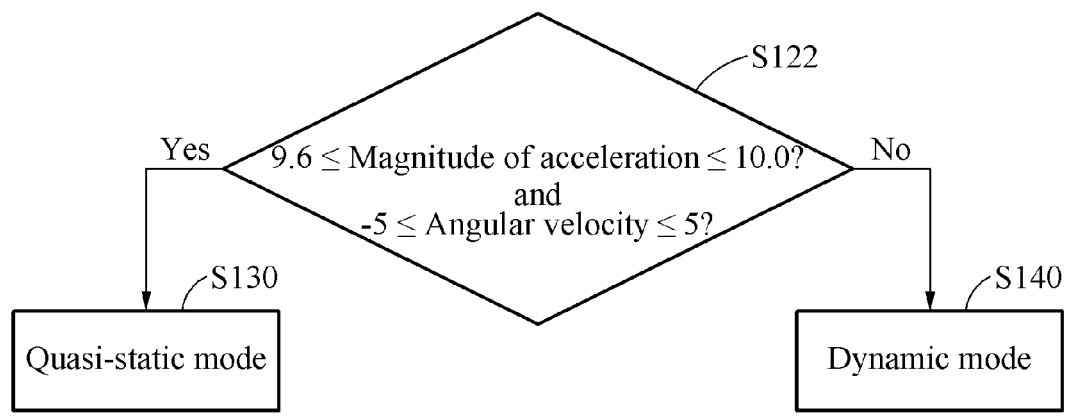
FIG. 6 is a flowchart illustrating an example of determining a quasi-static mode or a dynamic mode according to an example embodiment.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, descriptions of features that are known in the art may be omitted for increased clarity and conciseness.

Terms such as first, second, A, B, (a), (b), and the like may be used herein to describe components. Each of these terminologies is not used to define an essence, order, or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application. Also, in the description of embodiments, detailed description of well-known related structures or functions will be omitted when it is deemed that such description will cause ambiguous interpretation of the present disclosure.

Referring to FIGS. 1 through 8, a spasticity evaluation system 1 is used to measure a joint angle and a spasticity time by repeatedly turning or rotating a distal end portion of a human body with respect to a joint of the body by a user, and display a spasticity evaluation score using an evaluation tool. Although FIG. 1 illustrates the user rotating a shank with respect to a knee joint of the body, examples are not limited to the illustrated example. Thus, it may also be used to rotate a lower arm with respect to an elbow joint or rotate a foot with respect to an ankle joint. The spasticity evaluation system 1 includes a first sensor 11, a second sensor 12, a processor 13, and a display 14.

The first sensor 11 is configured to measure an acceleration of a distal end portion D connected to a joint J of a human body H, or an angular velocity of the distal end portion D. For such measurement, the first sensor 11 is attached to the distal end portion D classified based on the joint J of the human body H. For example, the first sensor 11 may be an inertial sensor or an inertial measurement unit (IMU) configured to measure accelerations, for example, $ax_1$, $ay_1$, and $az_1$, in three axial directions, for example, $x_1$, $y_1$, and $z_1$, respectively, or measure angular velocities, for example, $wx_1$, $wy_1$, and $wz_1$, in the three axial directions, respectively. The first sensor 11 is configured to measure two accelerations $ax_1$ and $ay_1$ in respective directions that are parallel to a sagittal plane and intersect each other, and an acceleration $az_1$ in a direction intersecting the sagittal plane. That is, the first sensor 11 is configured to measure a first acceleration $ax_1$ which is an acceleration in a first direction intersecting a length direction of the distal end portion D, a second acceleration $ay_1$ which is an acceleration in a second direction being the length direction of the distal end portion D, and a third acceleration $az_1$ which is an acceleration in a third direction intersecting the sagittal plane and intersecting each of the first acceleration $ax_1$ and the second acceleration $ay_1$. In addition, the first sensor 11 is configured to measure a first angular velocity $wx_1$ which is an angular velocity in the first direction, a second angular velocity $wy_1$ which is an angular velocity in the second direction, and a third angular velocity $wz_1$ which is an angular velocity in the third direction.

The second sensor 12 is attached to a proximal portion P classified based on the joint J of the human body H. Similar to the first sensor 11, the second sensor 12 is configured to measure an acceleration, for example, $ax_2$, $ay_2$, and $az_2$, in each of three axial directions, for example, $x_2$, $y_2$, and $z_2$, of the proximal portion P or measure an angular velocity, for example, $wx_2$, $wy_2$, and $wz_2$, in each of the three axial directions.

The processor 13 is configured to evaluate spasticity by applying an evaluation tool mainly used in a clinical field of application based on the measured accelerations or the measured angular velocities. Although FIG. 3 illustrates an example of an application of modified tardieu scale (MTS), examples are not limited to the illustrated example and other evaluation tools may also be used. The example of the application of MTS will be described herein.

According to the MTS, a user, for example, a doctor, a rehabilitator, and the like, may turn or rotate the distal end portion D of the human body H with respect to the joint J at three velocities $V_1$, $V_2$, and $V_3$ while a hip joint HJ of the human body H is being fixed. The three velocities $V_1$, $V_2$, and $V_3$ may be set in advance by the user based on a physical condition of the human body H, an evaluation method, and the like. The first velocity $V_1$ is defined as a lowest velocity, the second velocity $V_2$ is defined as a velocity at which a portion of the human body H, for example, the distal end portion D, falls, and the third velocity $V_3$ is defined as a high velocity greater than that of a free fall. Under such condition, when the user turns or rotates the distal end portion D of the human body H with respect to the joint J at the first velocity $V_1$, the user may measure an operating angle $R_2$ which is an operating range of the joint J. In addition, when the user turns the distal end portion D of the human body H with respect to the joint J at the second velocity $V_2$ or the third velocity $V_3$, the user may measure a catch angle $R_1$ which is an operating range of the joint J at a spasticity time $T_R$ at which resistance is applied to a movement of the distal end portion D.

The processor 13 includes a first velocity mode to determine the operating angle $R_2$, and a second velocity mode to determine the catch angle $R_1$. In detail, the processor 13 is configured to calculate the angular velocities measured by the first sensor 11 and the second sensor 12, or for example, add the angular velocities, and determine a result of the calculating to be a velocity of the joint J, for example, an angular velocity of the joint J. When an angular velocity of the joint J measured in the first velocity mode is the first velocity $V_1$, the processor 13 may determine, to be the operating angle $R_2$, a joint angle with a greatest magnitude among angles φ of the joint J. Here, an angle φ of the joint J, or a joint angle φ, is an acute angle among angles formed between the proximal portion P and the distal end portion D. When an angular velocity of the joint J measured in the second velocity mode is the second velocity $V_2$ or the third velocity $V_3$ which is greater than the first velocity $V_1$, the processor 13 may determine, to be the catch angle $R_1$, an angle φ of the joint J at the spasticity time $T_R$. That is, the processor 13 may determine, to be the catch angle $R_1$, a joint angle φ at a point in time at which a magnitude of a variation in measured angular velocity is maximum, for example, a point in time at which angular deceleration is maximum. In addition, when a time interval from a point in time of an initial state in which the distal end portion D starts moving to a point in time at which a magnitude of a variation in measured angular velocity is maximum is less than a preset reference time interval, the processor 13 may determine, to be the catch angle $R_1$, a joint angle φ at a point in time at which the magnitude of the variation in measured angular velocity is maximum, in order to determine the catch angle $R_1$. For example, the reference time interval may be set to be approximately 1 second. In addition, the processor 13 may determine whether the second velocity $V_2$ or the third velocity $V_3$ reaches a target velocity to determine the catch angle $R_1$. Here, the three velocities $V_1$, $V_2$, and $V_3$ may be set in advance in the processor 13 by the user based on a physical condition, an evaluation method, and the like. Through this, a spasticity situation in which a movement of the distal end portion D is subjected to resistance may be accurately applied to the processor 13, and thus accuracy and reliability of evaluation may be ensured.

The processor 13 is configured to determine a spasticity evaluation score based on the operating angle $R_2$, the catch angle $R_1$, and the spasticity time $T_R$. For example, when the spasticity time $T_R$ is 8 seconds and the catch angle $R_1$ is a value, for example, approximately 112°, a quality of muscle reaction may be evaluated to be a score of 3.

The processor 13 is configured to determine a joint angle φ formed between the distal end portion D and the proximal portion P based on the measured accelerations or the measured angular velocities. In detail, in operation S110, the processor 13 determines whether an acceleration ($az_1$, $az_2$) in a direction intersecting the sagittal plane of the human body H is included in the measured accelerations. In operation S120, the processor 13 determines a quasi-static mode or a dynamic mode based on the measured accelerations and the measured angular velocities. In operation S130, the processor 13 calculates an angle formed by the distal end portion D and the proximal portion P with respect to a coronal plane based on an acceleration measured in the quasi-static mode. In operation S140, the processor 13 calculates an angle by which the distal end portion D and the proximal portion P are rotated with respect to the coronal plane based on an angular velocity measured in the dynamic motion. In operation S150, the processor 13 determines a joint angle φ based on the angle calculated in each of the quasi-static mode and the dynamic mode.

The processor 13 determines whether an acceleration ($az_1$, $az_2$) in a direction intersecting the sagittal plane is included in the measured accelerations in operation S110. When the acceleration ($az_1$, $az_2$) in the direction intersecting the sagittal plane occur is included, the processor 13 performs a rotation transformation matrix Rzxy on the measured acceleration in operation S112. The rotation transformation matrix Rzxy refers to a matrix that transforms the acceleration ($az_1$, $az_2$) in the direction intersecting the sagittal plane into 0, and simultaneously corrects accelerations ($ax_1$, $ay_1$; $ax_2$, $ay_2$) which are parallel to the sagittal plane and intersect each other. Through this, irrespective of whether the first sensor 11 and/or the second sensor 12 are disposed at the distal end portion D and/or the proximal portion P, respectively, in a direction parallel to the sagittal plane, it is possible to correct the first sensor 11 and/or the second sensor 12 to be respectively arranged in the distal end portion D and/or the proximal portion P in the direction parallel to the sagittal plane and thus accurately calculate a joint angle φ, thereby improving accuracy and reliability of evaluation.

The processor 13 is configured to determine an attachment state of the first sensor 11 and an attachment state of the second sensor 12 based on the measured accelerations and the measured angular velocities. The processor 13 is configured to determine whether the acceleration ($az_1$, $az_2$) in the direction intersecting the sagittal plane is included in the measured accelerations. When the acceleration ($az_1$, $az_2$) in the direction intersecting the sagittal plane is included, the processor 13 is configured to determine the attachment state of the first sensor 11 and/or the second sensor 12 to be normal or abnormal. For example, the processor 13 may determine whether each of a magnitude of the acceleration $az_1$ in the third direction and a magnitude of the acceleration $az_2$ in the sixth direction is included in a preset magnitude range.

The processor 13 is configured to determine the quasi-static mode or the dynamic mode based on the measured accelerations and the measured angular velocities in operation S120. The quasi-static mode is defined as a mode to determine a joint angle φ based on the measured accelerations, and the dynamic mode is defined as a mode to determine a joint angle φ based on the measured angular velocities. In detail, when a magnitude of a measured acceleration ($a_1$; $a_2$) is in a first range, and a measured angular velocity ($wz_1$; $wz_2$) is in a second range, the processor 13 may determine the quasi-static mode, and otherwise, determine the dynamic mode in operation S122. For such determination, the processor 13 is configured to determine a variation in acceleration and a variation in angular velocity based on the measured accelerations and the measured angular velocities, respectively. When each of the variation in acceleration and the variation in angular velocity is less than a preset reference value, the processor 13 may determine the quasi-static mode. For example, the first range may be set to be from approximately 9.6 m/s² or greater to 10.0 m/s² or less, and the second range may be set to be from approximately −5 rad/s or greater to 5 rad/s or less. Through this, when a magnitude of the measured acceleration ($a_1$; $a_2$) is close to approximately 9.81 m/s² which is a magnitude of gravitational acceleration, and when the magnitude of the measured angular velocity ($wz_1$; $wz_2$) is within approximately 5 rad/s, it is considered that a velocity of the proximal portion P or the distal end portion D of the human body H is maintained consistently. Thus, when an acceleration changes continuously, it is more accurate to determine a result value by determining a joint angle φ based on an angular velocity in the dynamic mode than by determining a joint angle φ based on an acceleration in the quasi-static mode. Thus, it is possible to improve accuracy and reliability of evaluation.

The processor 13 is configured to calculate the angle formed by the distal end portion D and the proximal portion P with respect to the coronal plane based on the acceleration measured in the quasi-static mode in operation S130, and calculate the angle by which the distal end portion D and the proximal portion P are rotated with respect to the coronal plane based on the angular velocity measured in the dynamic mode in operation S140.

In the quasi-static mode, the processor 13 is configured to obtain a first angle θ1 which is an angle formed by the distal end portion D with respect to the coronal plane based on the first acceleration $ax_1$ and the second acceleration $ay_1$. In addition, the processor 13 is configured to obtain a second angle θ2 which is an angle formed by the proximal portion P with respect to the coronal plane based on the fourth acceleration axe and the fifth acceleration aye. In detail, the first angle θ1 and the second angle θ2 may be determined as represented by the following equation.

$$\theta_i = \tan^{-1}\left(\frac{ax_i}{ay_i}\right) \qquad <\text{Equation 1}>$$

(where, $i = 1, 2$).

Based on Equation 1, the first angle $\theta_1$ may be obtained by calculating an arctangent with a value obtained by dividing, by the second acceleration $ay_1$, the first acceleration $ax_1$ on the sagittal plane among the accelerations measured by the first sensor 11. Similarly, the second angle $\theta 2$ may be obtained by calculating an arctangent with a value obtained by dividing, by the fifth acceleration $aye$, the fourth acceleration $ax_2$ on the sagittal plane among the accelerations measured by the second sensor 12.

In the dynamic mode, the processor 13 is configured to obtain a first angular displacement $\theta_1$ by performing an integration on the angular velocity $wz_1$ measured by the first sensor 11. In addition, the processor 13 is configured to obtain a second angular displacement $\theta_2$ by performing an integration on the angular velocity $wz_2$ measured by the second sensor 12. In detail, the first angular displacement $\theta_1$ and the second angular displacement $\theta_2$ may be determined as represented by the following equation.

$$\theta_i = \int w_i(t)dt + \theta_{lastest,i} \qquad <\text{Equation 2}>$$

The processor 13 determines a joint angle $\varphi$ based on the angles calculated in the quasi-static mode and the dynamic mode, respectively, in operation S150. In detail, the joint angle $\varphi$ may be determined as represented by the following equation.

$$\theta_{joint} = \theta_1 + \theta_2 \qquad <\text{Equation 3}>$$

(where, $\theta_{joint}$ denotes the joint angle $\varphi$, and $\theta_1$ denotes the first angle or the first angular displacement and $\theta_2$ denotes the second angle or the second angular displacement.)

Through this, by modeling each of the distal end portion D and the proximal portion P of the human body H as a link connected to a joint between the fixed hip joint HJ and the joint J, it is possible to readily calculate a joint angle $\varphi$ and also ensure accuracy, thereby improving accuracy and reliability of evaluation. In addition, it is possible to significantly increase a speed of the calculation, and thus ensure rapidity of the evaluation.

A fundamental concept of determining a joint angle $\varphi$ described above may be applied to various examples. However, the description provided above may be merely about a method used to determine a joint angle $\varphi$, and thus examples are not necessarily limited to the foregoing description.

Figure 7:
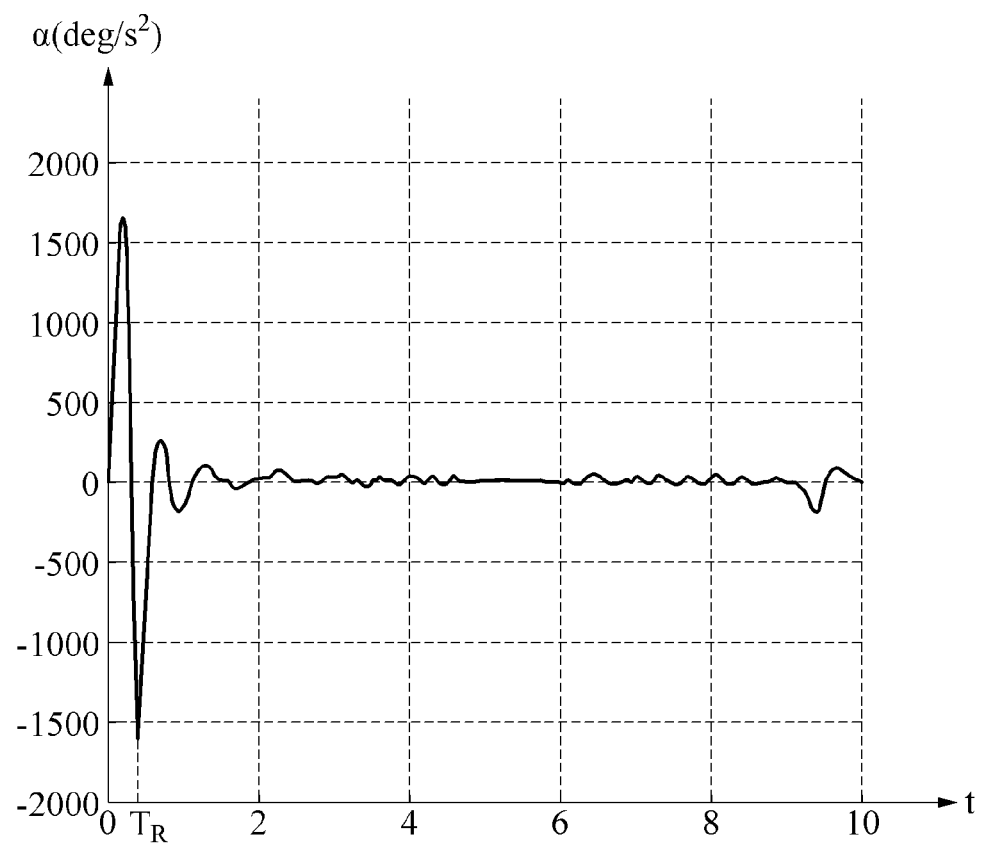
FIG. 7 is a graph illustrating an example of determining a spasticity time according to an example embodiment.
Figure 8:
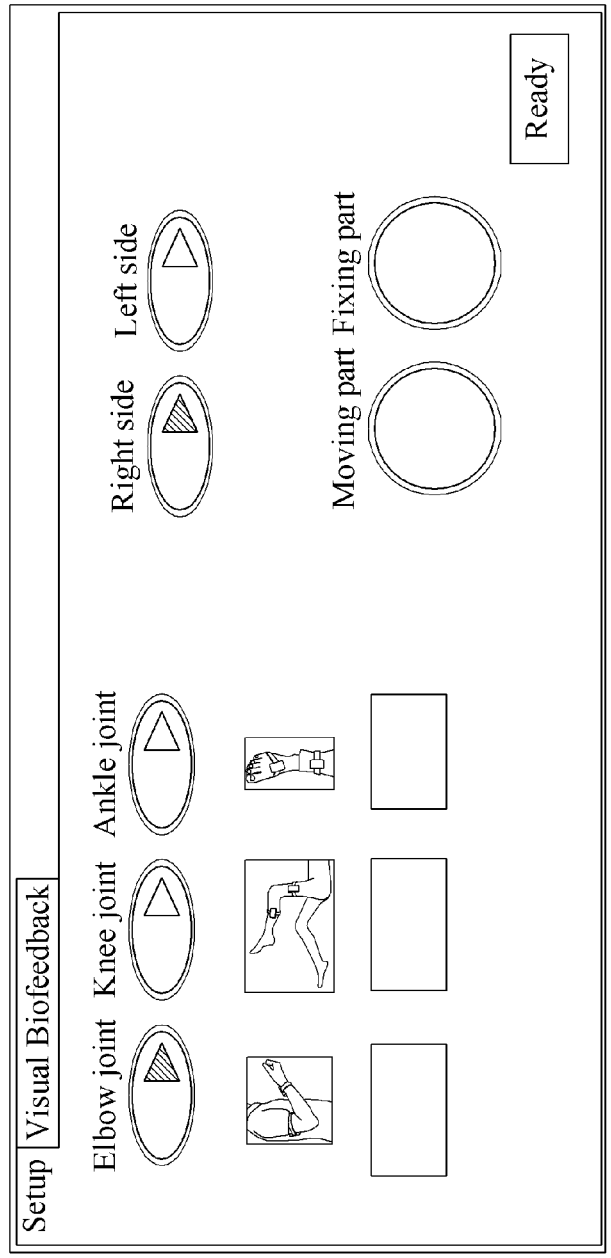
FIG. 8 is a diagram illustrating an example of a display according to an example embodiment.
Figure 9:
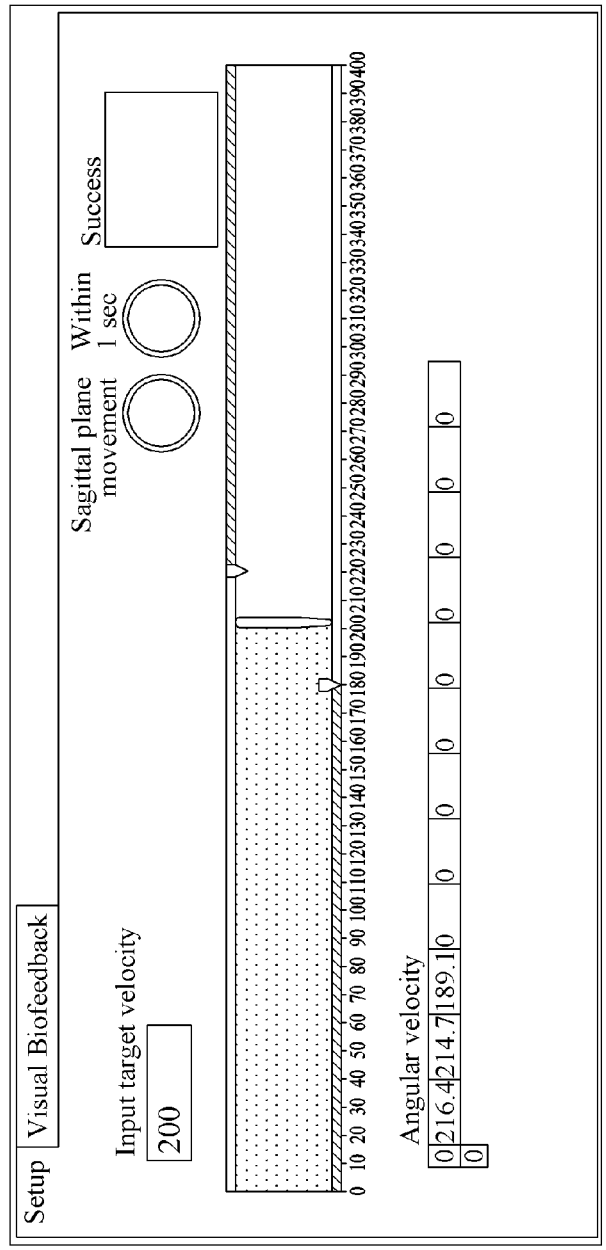
FIG. 9 is a diagram illustrating another example of a display according to an example embodiment.

The processor 13 is configured to determine the spasticity time $T_R$ at which a movement of the distal end portion D is subjected to resistance. FIG. 7 illustrates a graph of a variation in angular velocity over time, for example, an angular acceleration. The processor 13 is configured to set, to be an angular acceleration in a y-axis direction, a variation in angular velocity obtained by performing differentiation on the angular velocities measured by the first sensor 11 or the second sensor 12. Here, a time at a variation in angular velocity with a maximum magnitude, for example, a time at an angular acceleration with a maximum magnitude, may be determined to be the spasticity time $T_R$. Through this, when spasticity occurs while the user is turning the distal end portion D with respect to the joint J at the second velocity $V_2$ or the third velocity $V_3$, the distal end portion D of the human body H may not be turned any longer at the second velocity $V_2$ or the third velocity $V_3$, and a point in time at which velocity decreases rapidly may occur. Here, by determining, to be the spasticity time $T_R$, the point in time at which the velocity decreases rapidly, it is possible to ensure accuracy and reliability in setting the spasticity time $T_R$ and thus correctly perform evaluation of spasticity.

In addition, in a case of clonic convulsion, not being muscular rigidity, the processor 13 may determine an angle at which a movement or motion of the distal end portion D starts trembling and a start point at which the trembling is started, and process convulsion evaluation information for the clonic convulsion.

The display 14 is configured to display spasticity evaluation information to evaluate spasticity based on the joint angle $\varphi$ and the spasticity time $T_R$. The display 14 is configured to provide the spasticity evaluation information by two types, for example, setup and visual biofeedback.

The display 14 may allow the user to select, from a setup screen, whether to turn a distal end portion with respect to an elbow joint, a knee joint, or an ankle joint of a human body. In addition, the display 14 may allow the user to select, from the setup screen, whether to attach the first sensor 11 and the second sensor 12 to a right side or a left side of the human body. In addition, the display 14 may display, on the setup screen, a warning signal relating to an erroneous sensor attachment based on whether an attachment state of the first sensor 11 and/or an attachment state of the second sensor 12 is normal or abnormal. For example, when the first sensor 11 is attached to a moving part, for example, a shank, and the second sensor 12 is attached to a fixed part, for example, a thigh, and the attachment state of the first sensor 11 is normal and the attachment state of the second sensor 12 is abnormal, the display 14 may display a blue signal indicating that the attachment state of the first sensor 11 is normal and display a red signal indicating that the attachment state of the second sensor 12 is abnormal. Through this, the user may intuitively recognize the attachment state of the first sensor 11 and/or the second sensor 12 when using the spasticity evaluation system 1, and thus correctly attach the first sensor 11 and/or the second sensor 12 to corresponding locations. Thus, it is possible to improve accuracy and reliability of evaluation.

In addition, the display 14 may display a target velocity input by the user on a visual biofeedback screen. In addition, the display 14 may display whether a determined velocity of the joint J reaches the target velocity within a margin of error. Here, the margin of error may be set variously based on an environment in which the user uses the spasticity evaluation system 1, a characteristic of the human body H, and the like. For example, when the velocity of the joint J reaches a velocity with an approximately 10% margin of error from the target velocity, the display 14 may display a blue signal indicating that the velocity of the joint J reaches the target velocity. In addition, the display 14 may display, in real time, a velocity of the joint J and the target velocity in a form of bar graph, numeral, and the like. In addition, the display 14 may display whether the first sensor 11 and/or the second sensor 12 is accurately aligned and attached to the distal end portion D and/or the proximal portion P. For example, when there is no acceleration in a direction intersecting the sagittal plane among the accelerations measured by the first sensor 11 and/or the second sensor 12, the display 14 may display a blue signal to indicate whether there is a sagittal plane movement. In addition, the display 14 may display whether a time interval from a point in time of an initial state in which the distal end portion D starts moving to a point in time at which a magnitude of a variation in measured angular velocity is a maximum value is less than a preset reference time interval. For example, the reference time interval may be set to be within one second. When the time interval from the point in time of the initial state in which the distal end portion D starts moving to the point in time at which a magnitude of the variation in measured angular velocity is a maximum value is within one second, the display 14 may display a blue signal as to whether the time interval is within one second. In addition to the displaying of the blue signal relating to the sagittal plane movement or the time interval being within one second, the display 14 may display whether correct evaluation of spasticity is performed successfully or unsuccessfully when the two conditions are satisfied. For example, when the two conditions are satisfied, the display 14 may display a blue signal indicating that the evaluation of spasticity is performed successfully, and display a value of angular velocities accumulated by the time of the success. Through this, when the user users the spasticity evaluation system 1, the user may intuitively verify, in real time, a current joint velocity and whether the joint velocity reaches the target velocity or not, and receive, in real time, feedback on whether the evaluation is performed smoothly. Thus, accuracy and reliability of the evaluation may be improved.

In addition, the spasticity evaluation system 1 may include a communication module (not shown). The communication module may transfer, to the processor 13 and/or the display 14, inertial information including an acceleration or an angular velocity measured by the first sensor 11 and/or the second sensor 12. The communication module may be, for example, a Bluetooth module that enables short-range wireless communication.

The configurations and functions described above may be provided to an example of the spasticity evaluation system 1. The processor 13 and/or the display 14 may be embedded in the first sensor 11 and/or the second sensor 12. In such a case, such configuration may be embodied by a spasticity evaluation device. That is, the spasticity evaluation device may include a first sensor 11, a second sensor 12, and a display 14. Here, the display 14 may be provided in a form of a terminal, and a processor may be provided in a form of an application and perform the functions described above. The display 14 may display an attachment state of the first sensor 11 and/or an attachment state of the second sensor 12 and display, in real time, a current velocity, or angular velocity, of a joint, and a target velocity.

Figure 10:
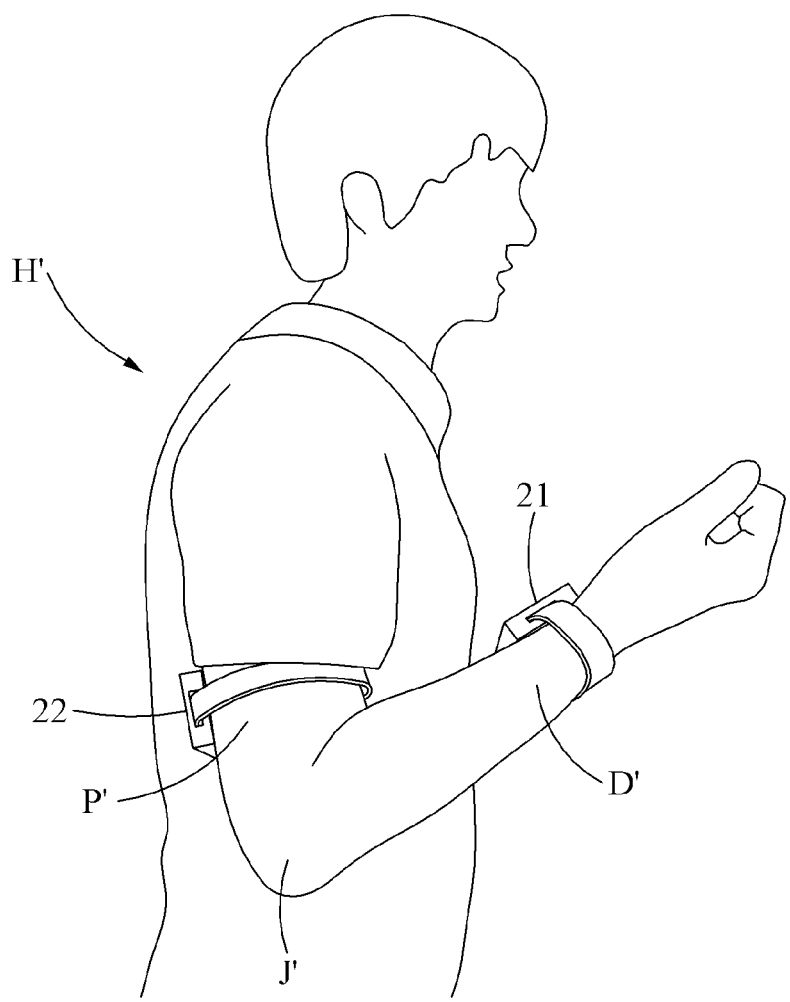
FIG. 10 is a diagram illustrating an example of a spasticity evaluation device and system according to an example embodiment.

Referring to FIG. 10, a spasticity evaluation device or system 2 includes a first sensor 21, a second sensor 22, and a display (not shown). In such a case, a processor may be embedded in the first sensor 21 and/or the second sensor 22, or separately provided. As illustrated, the first sensor 21 may be attached to a lower arm D' and the second sensor 22 may be attached to an upper arm P', with respect to an elbow joint J'.

Figure 11:
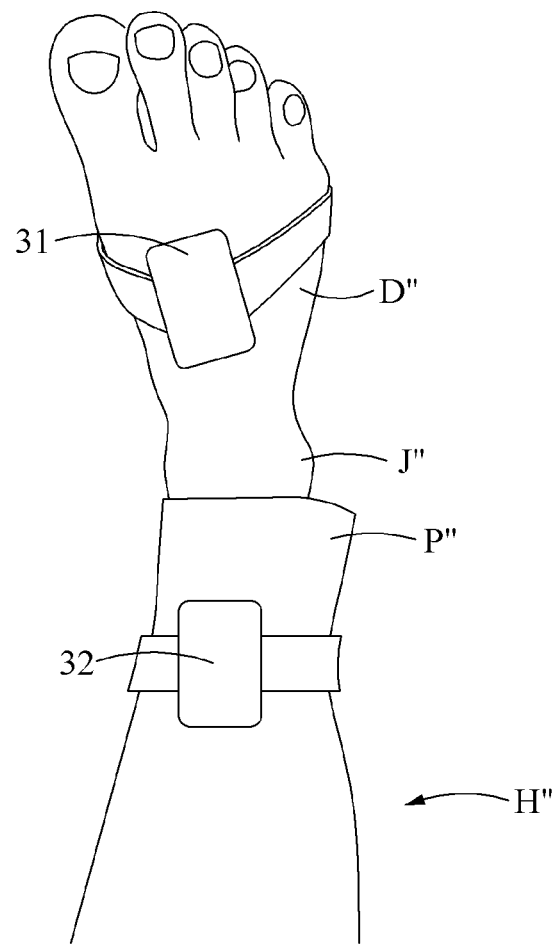
FIG. 11 is a diagram illustrating another example of a spasticity evaluation device and system according to an example embodiment.

Referring to FIG. 11, a spasticity evaluation device or system 3 includes a first sensor 31, a second sensor 32, and a display (not shown). As illustrated, the first sensor 31 may be attached to a top of a foot D" and the second sensor 32 may be attached to an ankle P", with respect to an ankle joint J".

Example embodiments include non-transitory computer-readable media including program instructions to implement various operations embodied by a computer. The media may also include, alone or in combination with the program instructions, data files, data structures, tables, and the like. The media and program instructions may be those specially designed and constructed for the purposes of example embodiments, or they may be of the kind well known and available to those having skill in the computer software arts. Examples of non-transitory computer-readable media include magnetic media such as hard disks, floppy disks, and magnetic tape; optical media such as CD ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter. The described hardware devices may be configured to act as one or more software modules in order to perform the operations of the above-described example embodiments, or vice versa.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A spasticity evaluation system comprising:
   a first sensor configured to be attached to a distal end portion of a human body from a joint of the human body, and configured to measure at least one of an acceleration of the distal end portion or an angular velocity of the distal end portion;
   a second sensor configured to be attached to a proximal portion of the human body from the joint of the human body, and configured to measure at least one of an acceleration of the proximal portion or an angular velocity of the proximal portion;
   a processor configured to
      determine an angle of the joint formed between the distal end portion and the proximal portion based on a quasi-static mode in which the angle of the joint is determined based on measured accelerations of the distal end portion and the proximal portion and a dynamic mode in which the angle of the joint is determined based on measured angular velocities of the distal end portion and the proximal portion, and determine the quasi-static mode or the dynamic mode based on the measured accelerations of the distal end portion and the proximal portion and the measured angular velocities of the distal end portion and the proximal portion, and
      determine a spasticity time based on determining a resistance has been applied to a movement of the distal end portion; and
   a display configured to display spasticity evaluation information to be used to evaluate spasticity based on the angle of the joint and the spasticity time.

2. The spasticity evaluation system of claim 1, wherein, based on the measured accelerations including an acceleration occurring in a direction intersecting a sagittal plane of the human body, the processor is configured to determine the angle of the joint by performing a rotation transformation matrix on the measured accelerations.

3. The spasticity evaluation system of claim 1, wherein, based on a magnitude of the measured accelerations being in a first range and a magnitude of the measured angular velocities being in a second range, the processor is configured to determine the quasi-static mode.

4. The spasticity evaluation system of claim 1, wherein, based on the quasi-static mode being determined, the processor is configured to obtain a first angle based on a first acceleration occurring in the same direction as a sagittal plane of the human body among accelerations measured by the first sensor and a second acceleration in a direction intersecting a direction of the first acceleration occurring in the same direction as the sagittal plane, obtain a second angle based on a fourth acceleration occurring in the same direction as the sagittal plane among accelerations measured by the second sensor and a fifth acceleration in a direction intersecting a direction of the fourth acceleration occurring in the same direction as the sagittal plane, and determine the angle of the joint based on the obtained first angle and the obtained second angle.

5. The spasticity evaluation system of claim 1, wherein, based on the dynamic mode being determined, the processor is configured to obtain a first angular displacement by performing an integration on angular velocities measured by the first sensor, obtain a second angular displacement by performing an integration on angular velocities measured by the second sensor, and determine the angle of the joint based on the obtained first angular displacement and the obtained second angular displacement.

6. The spasticity evaluation system of claim 1, wherein the processor is configured to calculate a magnitude of a variation in angular velocity measured by the first sensor or a magnitude of a variation in angular velocity measured by the second sensor, and determine, to be the spasticity time, a point in time corresponding to a variation with a maximum magnitude among the calculated magnitudes of the variation.

7. The spasticity evaluation system of claim 1, wherein the processor is further configured to
based on the measured angular velocities being a first velocity, a first velocity mode in which an angle of the joint with a maximum magnitude is determined to be an operating velocity; and
based on the measured angular velocities being a second velocity which is greater than the first velocity, a second velocity mode in which an angle of the joint at the spasticity time is determined to be a catch angle.

8. The spasticity evaluation system of claim 7, wherein the processor is configured to determine a spasticity evaluation score in the spasticity evaluation information based on the operating angle, the catch angle, and the spasticity time.

9. The spasticity evaluation system of claim 1, wherein the first sensor is configured to measure an acceleration in a length direction of the distal end portion occurring in the same direction as a sagittal plane of the human body, an acceleration in a direction intersecting the length direction of the distal end portion occurring in the same direction as the sagittal plane, and an angular velocity in a direction intersecting the sagittal plane.

10. The spasticity evaluation system of claim 1, wherein the processor is configured to determine an attachment state of the first sensor and an attachment state of the second sensor based on at least one of the measured accelerations or the measured angular velocities, and the display is configured to display a warning signal relating to an erroneous sensor attachment based on the determined attachment state of the first sensor and the determined attachment state of the second sensor.

11. The spasticity evaluation system of claim 1, wherein the processor is configured to determine a velocity of the joint based on the measured accelerations or the measured angular velocities, and
the display is configured to display whether the velocity of the joint reaches a target velocity within a preset margin of error.

12. A spasticity evaluation device comprising:
a first sensor configured to be attached to a distal end portion of a human body from a joint of the human body, and configured to obtain a first measurement value including at least one of an acceleration in a first direction intersecting a length direction of the distal end portion, an acceleration in a second direction intersecting the first direction, or an angular velocity in a third direction intersecting each of the first direction and the second direction;
a second sensor configured to be attached to a proximal portion of the human body from the joint of the human body, and configured to obtain a second measurement value including at least one of an acceleration in a fourth direction intersecting a length direction of the proximal portion, an acceleration in a fifth direction intersecting the fourth direction, or an angular velocity in a sixth direction intersecting each of the fourth direction and the fifth direction;
a processor configured determine an angle of the joint based on a quasi-static mode in which the angle of the joint is determined based on the measured accelerations of the distal end portion and the proximal portion and a dynamic mode in which the angle of the joint is determined based on the measured angular velocities of the distal end portion and the proximal portion, and determine the quasi-static mode or the dynamic mode based on the measured accelerations and the measured angular velocities; and
a display connected to the first sensor and the second sensor, and configured to display spasticity evaluation information to be used to evaluate spasticity based on the angle of the joint, the first measurement value, and the second measurement value.

13. The spasticity evaluation device of claim 12, wherein the display is configured to display, as a velocity of the joint, a value obtained by calculating the angular velocity in the third direction and the angular velocity in the sixth direction.

14. The spasticity evaluation device of claim 13, wherein the display is configured to display the velocity of the joint in real time, and display whether the velocity of the joint reaches a target velocity.

15. The spasticity evaluation device of claim 12, wherein the first measurement value further includes an acceleration in the third direction, and the second measurement value further includes an acceleration in the sixth direction,
wherein the display is configured to display whether each of a magnitude of the acceleration in the third direction and a magnitude of the acceleration in the sixth direction is included in a preset magnitude range.

16. A spasticity evaluation method comprising:
measuring
at least one of an acceleration or an angular velocity of a distal end portion of a human body from a joint of the human body, and at least one of an acceleration or an angular velocity of a proximal portion of the human body from the joint of the human body;

determining a quasi-static mode or a dynamic mode based on the measured accelerations of the distal end portion and the proximal portion and the measured angular velocities of the distal end portion and the proximal portion;

determining an angle of the joint based on an acceleration measured in the quasi-static mode, and determining the angle of the joint based on an angular velocity measured in the dynamic mode;

determining a spasticity time based on determining a resistance has been applied to a movement of the distal end portion; and determining a spasticity evaluation score based on the determined angle of the joint and the determined spasticity time.

17. The spasticity evaluation method of claim 16, after the measuring of the acceleration or the angular velocity of the distal end portion, and the acceleration or the angular velocity of the proximal portion, further comprising:

displaying a warning signal relating to an erroneous sensor attachment, based on each of an acceleration in a direction intersecting a sagittal plane of the human body among measured accelerations of the distal end portion, and an acceleration in a direction intersecting the sagittal plane among measured accelerations of the proximal portion is out of a preset magnitude range.

18. The spasticity evaluation method of claim 17, based on the displaying of the warning signal, further comprising:

determining an angular velocity of the joint by calculating the measured angular velocity of the distal end portion and the measured angular velocity of the proximal portion; and displaying whether the determined angular velocity of the joint reaches a target velocity.

19. The spasticity evaluation method of claim 16, before the determining of the quasi-static mode or the dynamic mode, further comprising:

performing a preset rotation transformation matrix on each of the measured acceleration of the distal end portion and the measured acceleration of the proximal portion, based on each of an acceleration component in a direction intersecting a sagittal plane of the human body among measured accelerations of the distal end portion and an acceleration component in a direction intersecting the sagittal plane among measured accelerations of the proximal portion is out of a preset magnitude range.

* * * * *